United States Patent
Büttner (10) Patent No.: US 7,340,354 B2
(45) Date of Patent: Mar. 4, 2008

(54) METHOD FOR DETECTION OF A STABLE INSTALLATION OF A SYSTEM HAVING A ROTATING DEVICE THEREIN

(75) Inventor: Thorsten Büttner, Kirchehrenbach (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/366,878

(22) Filed: Mar. 2, 2006

(65) Prior Publication Data

US 2006/0229845 A1    Oct. 12, 2006

(30) Foreign Application Priority Data

Mar. 2, 2005    (DE) .................. 10 2005 009 557

(51) Int. Cl.
*G01F 17/00*    (2006.01)
(52) U.S. Cl. ........................... 702/56; 702/179
(58) Field of Classification Search ............... 702/179, 702/56
See application file for complete search history.

(56) References Cited

U.S. PATENT DOCUMENTS

| | | | |
|---|---|---|---|
| 4,191,892 A * | 3/1980 | Huang et al. ................. 378/14 |
| 6,434,512 B1 * | 8/2002 | Discenzo .................... 702/184 |
| 6,590,960 B2 | 7/2003 | Kroener et al. |
| 2004/0060347 A1 | 4/2004 | Comperat et al. |

* cited by examiner

*Primary Examiner*—John Barlow
*Assistant Examiner*—Stephen J. Cherry
(74) *Attorney, Agent, or Firm*—Schiff Hardin LLP (57) ABSTRACT

In a method for detection of a stable installation of a system that has a rotation device mounted to rotate around a system axis and an arrangement for detection of measurement values indicative of oscillation of the rotation device, a statistical spread of the measurement values is calculated from N measurement values of different rotations of the rotation device, and the stable installation of the system is detected by a comparison of the calculated statistical spread with a predeterminable threshold. The detected N measurement values can be detected with a known arrangement for determination of an out-of-balance condition, so the method for detection of a stable installation can be implemented without the use of additional hardware components.

15 Claims, 5 Drawing Sheets

METHOD FOR DETECTION OF A STABLE INSTALLATION OF A SYSTEM HAVING A ROTATING DEVICE THEREIN

BACKGROUND OF THE INVENTION

1. Field of the Invention

The present invention concerns a method for detection of a stable installation (setup) of a system of the type having a rotation device that rotates around a system axis and a detection arrangement for measurement values of oscillation (vibration) of the rotation device. The invention moreover concerns a method for detection of a stable installation of a computed tomography system as a part of a method for correction of an out-of-balance state of the gantry thereof.

2. Description of the Prior Art

In apparatuses with rapidly rotating masses, an existing out-of-balance condition, or an out-of-balance condition that occurs in the course of the operation, lead to a series of unwanted events. These range from oscillations of the overall system to excessive bearing wear and, in medical apparatuses, to interferences in the generation of images, such as in medical tomography apparatuses.

A tomography apparatus of this type is, for example, a computed tomography apparatus with a rotation device in the form of a gantry, the rotation device being mounted to rotate around the system axis. An out-of-balance state can be caused, for example, by installation tolerances of the components on the gantry.

For detection and correction of an existing out-of-balance condition or an out-of-balance condition that occurs during the operation of the computed tomography apparatus from DE 101 08 065 A1 discloses an arrangement for detection of measurement values of an oscillation of the gantry caused by an out-of-balance situation. At least one point on the gantry at which a weight should be arranged for compensation of the out-of-balance state is determined from the detected measurement values.

The detected measurement values are influenced not only by the out-of-balance situation of the gantry itself but also by the oscillation behavior of the overall system. The measurement values can be significantly disturbed given an unstable installation of the computed tomography apparatus. An incorrect installation during the start-up can lead, for example, to the situation that the overall system additionally exhibits a barely perceivable tilt movement during the rotation of the gantry.

The location at which a weight should be arranged for compensation of the oscillation behavior in such a case is incorrectly determined on the basis of the disturbed measurement values. Even for experienced service personnel, it is not possible to correct the out-of-balance condition sufficiently well by an arrangement of weights on the gantry without correction of the installation of the computed tomography apparatus, even with multiple repetitions of the correction process.

SUMMARY OF THE INVENTION

It is an object of the present invention to provide a method that allows detection of stable installation of a system in a simple manner.

The above object is achieved in accordance with the invention by a method for detection of a stable installation of a system having a rotation device that rotates around a system axis and an arrangement for detection of measurement values of an oscillation of the rotation device including the step of detecting at least one measurement value set of N measurement values from N different rotations of the rotation device, automatically electronically calculating a statistical spread (scattering; distribution) per measurement value set from the N measurement values and making a threshold comparison between the statistical spread and a predeterminable threshold per measurement value set, the system being considered to be supported in a stable manner when the statistical spread for each measurement value set satisfies a predetermined relation to the threshold, e.g. is smaller than the threshold.

The detection of a stable installation of the system thus ensues on the basis of a calculation and evaluation of the statistical distribution of the detected measurement values from various rotation cycles of the rotation device, with the calculation and evaluation implemented in a simple manner. The measurement values can thereby be detected and evaluations by a measurement device that is already present in the system (for example a computed tomography apparatus) for correction of an out-of-balance state of the rotation device, such that no additional or special auxiliary equipment is required for implementation of the method.

In an embodiment of the method, two measurement value sets, each having N measurement values, are detected for two measurement planes, the measurement planes being perpendicular to the system axis and exhibiting an offset (spacing) relative to one another in the direction of the system axis. Due to the offset of the measurement planes in the direction of the system axis, it is possible to also correct dynamic imbalances (disequilibriums). Such dynamic imbalances always arise when the resulting inertial axis of the rotation device does not run parallel to the system axis or rotation axis.

Each measurement value is a vector with two vector components, the first vector component representing the magnitude of an out-of-balance state and the second vector component representing the angle of that out-of-balance state. To detect the stable installation of the system, the same measurement values that are conventionally generated for measurement of the out-of-balance condition of the rotation device are used, but they are further processed for evaluation of the stable installation of the system in accordance with the invention, so the stable installation can be determined without additional measurement effort.

Preferably, both vector components are converted into a Cartesian first measurement value component and a Cartesian second measurement value component. This enables a simple calculation of the statistical spread on the basis of the determined Euclidean distance.

The calculation of the statistical spread can include calculation of a first statistical spread from the first measurement value components and a calculation of a second statistical spread from the second measurement value components of the N measurement values of a measurement value set. In the simplest case, the first statistical spread is formed as a difference between a maximum value and minimum value of the first measurement value components. It is likewise possible for the second statistical spread to be determined in a simple manner as a difference between a maximum value and a minimum value of the second measurement value components. The statistical spread naturally also can be determined in the typical form of an average quadratic deviation from a determined expected value of the measurement values. It is only necessary for the statistical distribution of the measurement values to be mathematically determined in some appropriate manner.

In an embodiment of the invention, the aforementioned threshold includes a first threshold component and a second threshold component. The threshold comparison between the statistical spread and the threshold is then implemented separately for each component. The separate comparison of the first statistical spread of the first measurement value component with a first threshold and the comparison of the second statistical spread of the second measurement value component with a second threshold can be implemented with little effort. The thresholds typically are determined in advance by multiple measurements for a stable installation and for an unstable installation of the system.

The detection of a stable installation can be implemented for an imaging system, such as in the form of a computed tomography system. Such systems normally already include equipment for detection of an out-of-balance condition of the rotation device, so no additional hardware components are necessary.

The above-described method for detection of a stable installation of a computed tomography system can also be used as a portion of a method for correction of an out-of-balance condition of a gantry that includes steps of detecting a stable installation of the computed tomography system, and upon detection of a stable installation of the computed tomography system, continuing the correction of the out-of-balance condition of the gantry, and upon detection of an unstable installation of the computed tomography system, generating a warning signal.

After an acknowledgement of the warning signal by an operator, the correction of the out-of-balance condition continued in a further step, or the method is repeated from the beginning after correction of the instability of the computed tomography system.

DESCRIPTION OF THE PREFERRED EMBODIMENTS

Figure 1:
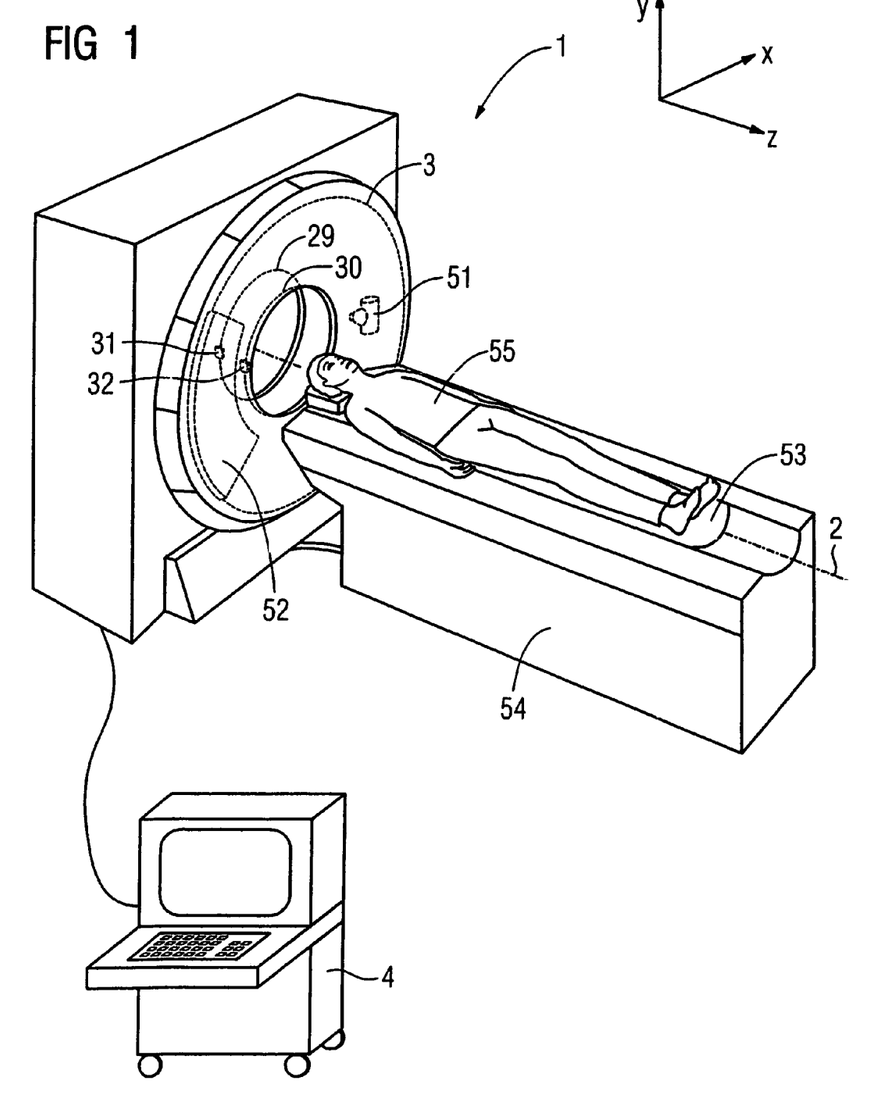
FIG. 1 schematically illustrates a computed tomography system implementing the inventive method.

FIG. 1 shows a system 1 (here a computed tomography system) with a rotation device in the form of a gantry, the rotation device being mounted such that it can rotate around a system axis 2.

A subject 55, for example a patient, can be supported on a displaceable table plate 53 of a support device 54 of the system 1, so the patient can be moved through an opening in the housing of the system 1 into a measurement region of an acquisition system associated with the rotation device 3.

The acquisition system includes an x-ray source 51 (for example an x-ray tube) and a detector 52 arranged opposite the x-ray source 51. The detector 52 contains a number of detector elements in columns and rows. The x-ray source 51 generates a fan-shaped x-ray beam. The x-ray beam penetrates the subject 55 positioned in the measurement region and strikes the detector elements of the detector 52. Each detector element generates an electrical attenuation value dependent on the attenuation of the x-ray radiation that has penetrated through the measurement region and struck that detector element. The conversion of the x-ray radiation into electrical attenuation values ensues, for example, by means of a photodiode optically coupled with a scintillator, or by means of a directly-transducing semiconductor. A set of attenuation values of the detector 52, which are acquired for a specific position of the x-ray source 51 relative to the subject 55, is known as a "projection".

The rotation device 3 is rotated around the system axis 2 of the system 1 with a high rotation speed in a known manner by a drive unit (not shown). A number of projections of the subject respectively from different projections directions can be produced in this manner. In particular, an examination region of the subject 55 that is larger than the measurement region formed by the acquisition system can be scanned by rotation of the rotation device 3 with simultaneous, continuous feed of the subject 55 in the direction of the system axis 2. The measurement values of the subject 55 acquired from various projection directions from such spiral-scanning can be calculated into slice or volume images and can be visually displayed on a display unit of an operating console.

In modern systems, rotation speeds of up to 180 revolutions/minute of the rotation device 3 are achieved. Even slight out-of-balance conditions cause oscillations (vibrations) that can lead to unwanted noise, excessive bearing wear to interferences in the generation of the images.

To avoid these unwanted occurrences, the system shown in FIG. 1 has components 4, 31, 32 for determination and correction of an out-of-balance state of the rotation device 3. These components include a sensor 31 that is mounted to obtain measurement value sets 5 and 6 in a measurement plane 29. The measurement value set 5 contains N measurement values 9 and the measurement value set 6 contains N measurement values 10. These components also include another sensor 32 that is mounted to obtain measurement value sets 7 and 8 in another measurement plane 30 that is spaced from the measurement plane 29. The measurement value set 7 contains N measurement values 11 and the measurement value set 8 contains N measurement values 12. The respective measurement values 9, 10, 11 and 12 in the respective measurement value sets 5, 6, 7 and 8 are obtained during different rotations of the rotation device 3, i.e., the rotation device 3 proceeds through N rotations during the acquisition of the measurement value sets 5, 6, 7 and 8. The measurement values 9, 10, 11, 12 are transmitted to a computer 4 for further processing.

The measurement planes 29, 30 are perpendicular to the system axis 2 and exhibit an offset (spacing) relative to one another in the direction of the system axis 2. On the basis of the detected measurement values 9, 10 and 11, 12 in the two measurement planes 29, 30, it is possible to determine the at least one position on the rotation device 3 at which a compensation weight of a specific mass must be placed so that the rotation device 3 rotates in a balanced manner.

The detected measurement values 9, 10, 11, 12 are influenced not only by the out-of-balance condition of the rotation device 3 itself, but also by the oscillation behavior of the overall system 1. In particular, given an unstable installation of the system 1, it can occur that the system 1 effects a barely perceptible tilting movement. In this case, the measurement values 9, 10, 11, 12 are severely disturbed by the oscillation behavior of the system 1, such that a correction of the out-of-balance condition of the rotation device 3 is not possible in principle. For this reason, in accordance with the present invention, further processing of the measurement values 9, 10, 11, 12 takes place to check the stable installation of the overall system 1 before beginning correction of the out-of-balance condition of the rotation device 3.

Figure 2:
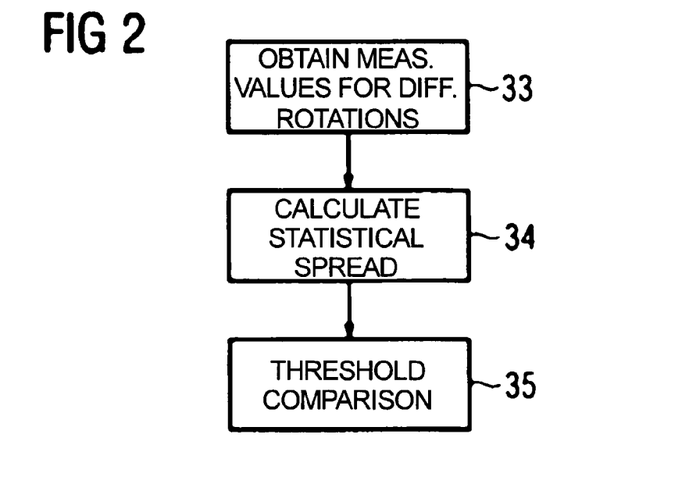
FIG. 2 is a flow chart of an embodiment of the inventive method for detection of a stable installation of a computed tomography system of the type shown in FIG. 1.

This proceeds as shown in FIG. 2. In a first method step 33, at least one measurement value set of N measurement values from N different rotations of the rotation device is acquired. In a second method step 34, a statistical spread is calculated for each measurement value set from the N measurement values thereof. In a third method step 35, a threshold comparison between the statistical spread and a predeterminable threshold is implemented for each measurement value set.

To detect a stable installation of the system 1, it may not be necessary for each individual measurement value to be processed. Instead, the measurement values can be averaged over several rotations before the further processing. In this manner anomalies that do not directly arise from the oscillation of the system can be suppressed.

A stable installation of the system 1 is assumed to exist when the statistical spread for each measurement value set is smaller than the threshold. Should it occur for at least one measurement value set that the statistical spread is greater than the threshold, it can be assumed with a high probability that the system is not supported in a stable manner.

Figure 3:
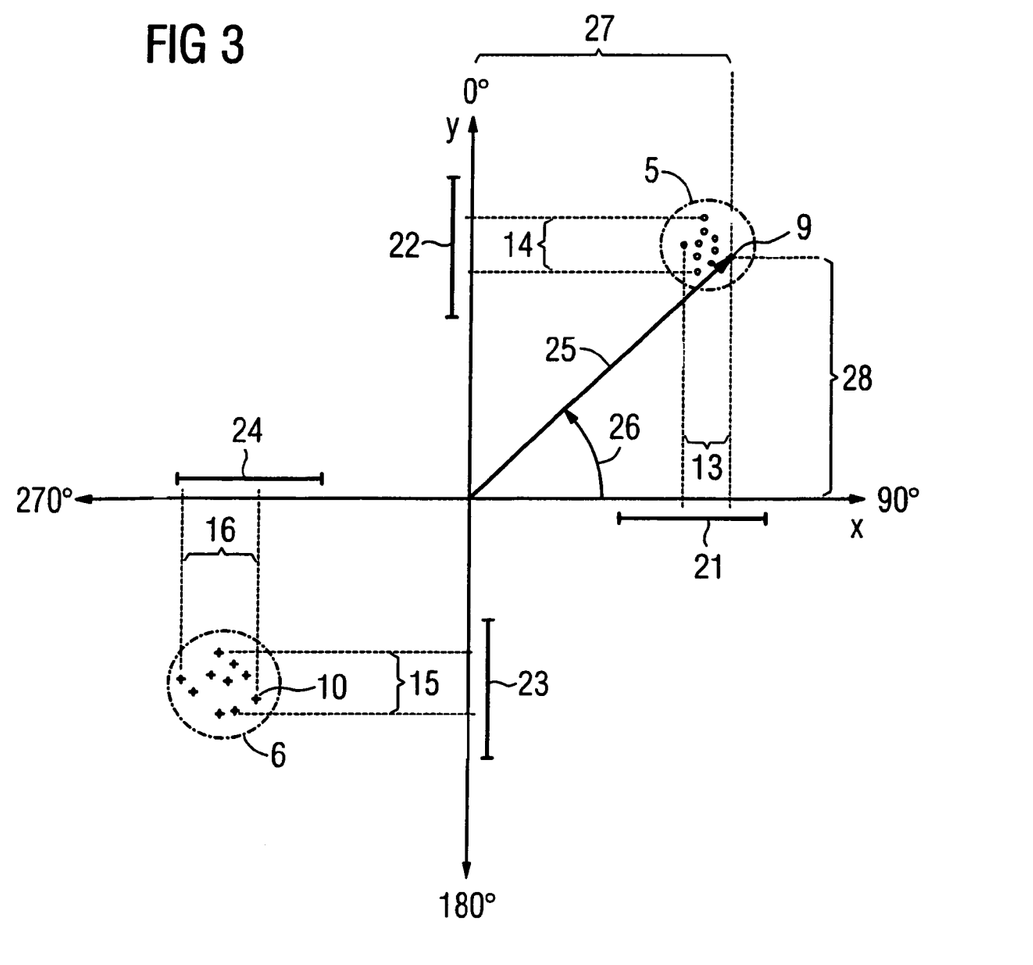
FIG. 3 is a diagram showing two measurement value sets from the two measurement planes shown in FIG. 1 of the rotation device for a stable installation of the computed tomography system.
Figure 4:
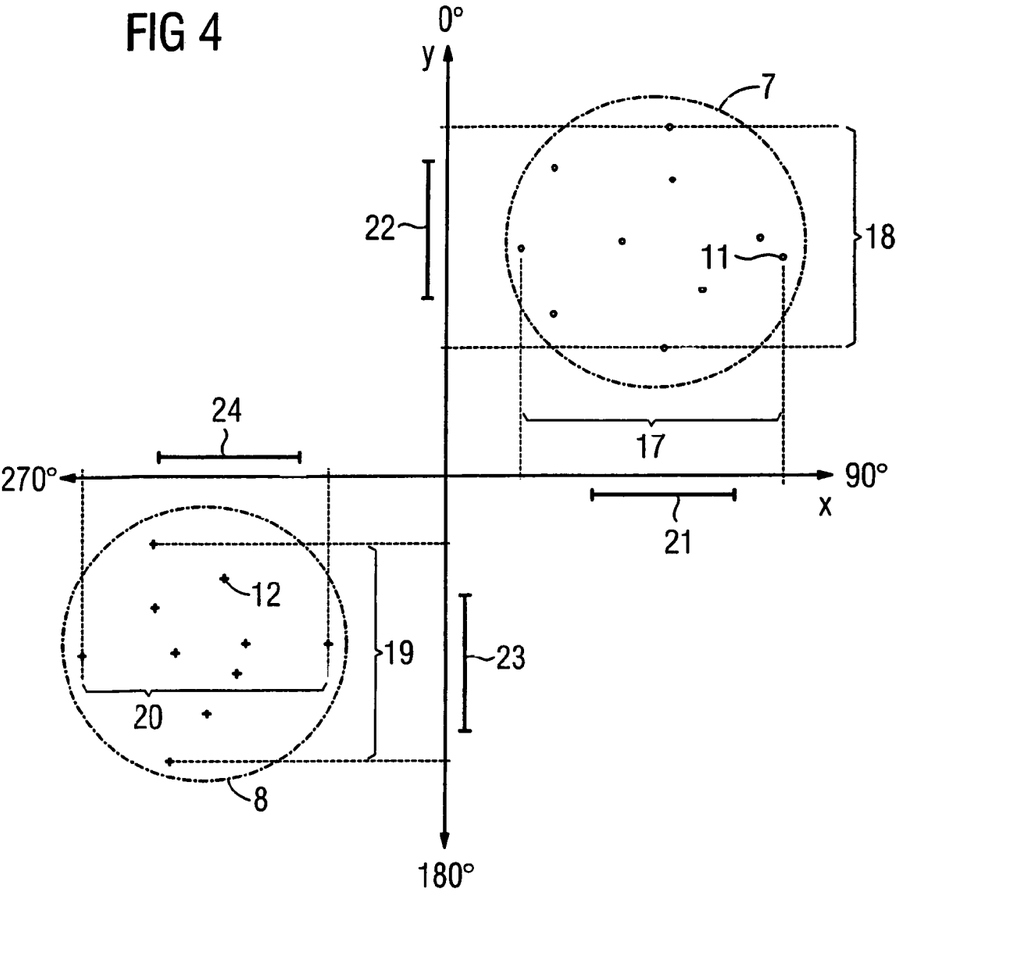
FIG. 4 is a diagram showing two measurement value sets from the two measurement planes shown in FIG. 1 of the rotation device for an unstable installation of the computed tomography system.

For explanation of this procedure, measurement value sets 5, 6, 7, 8 for detection of an out-of-balance condition for two different measurement situations are respectively shown in FIGS. 3 and 4.

FIG. 3 shows two detected measurement value sets 5, 6, respectively from the two measurement planes 31, 32 of the rotation device 3 for a stable installation of the system 1. In this example, the measurement value sets 5 and 6 respectively, contain measurement values 9 and 10, each composed of N=10 values. For clarity, only one measurement value is provided with a reference character in each measurement value set. The measurement values 9 of the first measurement value set 5 from the first measurement plane 29 are characterized by a circular symbol, and the measurement values 10 of the second measurement value set 6 from the second measurement plane 30 are characterized by a cross-shaped symbol.

A measurement value can be specified as a vector with two vector components. The first vector component 25 represents the magnitude of the out-of-balance condition and the second vector component 26 represents the angle of the out-of-balance condition. In FIG. 3, the measurement values 9, 10 are represented in Cartesian coordinates with a first measurement value component 27 in the x-direction and a second measurement value component 28 in the shown y-direction. The first measurement value component 27 and the second measurement value component 28 are indicated as examples only for one measurement value. The x- and y-directions thereby correspond to the axes of the coordinate system shown in FIG. 1. The translation of the measurement values 9, 10 into Cartesian coordinates has the advantage that a simple calculation of the statistical spread 13, 14, 15, 16 can be made on the basis of a Euclidean distance.

The measurement values 9 and 10 for a respective measurement planes 29 and 20 exhibit only a slight statistical spread 13, 14 and 15, 16, respectively, among one another in the case of a stable installation of the system 1. In the example, the first average value of the first measurement value set 5 is different from the second average value of the second measurement value set 6. In this case the out-of-balance condition is thus caused by a dynamic imbalance, because the resulting inertial axis does not run in parallel to the system axis 2; which is also the rotation axis of the rotation device 3.

In this example the calculation ensues separately for each measurement value set 5 and 6 and separately for each measurement value component 27 and 28. In the simplest case, the respective statistical spread is formed as a difference of a maximum and minimum value of the measurement value components 27 and 28 of the measurement values 9 and 10.

The statistical spread does not need to be calculated per component; rather, for example, it can be determined directly from the measurement values 9 and 10 or in a conventional manner as a variance, i.e., a measure of the average quadratic deviation of the measurement values 9 and 10 from an expected value.

Instead of the statistical spread 13, 14, 15, 16, other statistical parameters or characteristics or indicators are suitable for determination of the stable installation of the system 1. It is only necessary that the calculated statistical entries be amenable to mathematically describing the statistical distribution of the measurement values.

As a result of this calculation, four different statistical spreads 13, 14, 15, 16 are obtained, namely the first and second statistical spreads 13, 14 of the first and second measurement value components 27, 28 of the measurement values 9 of the first measurement value set 5, and first and second statistical spreads 15, 16 of the first and second measurement value components 27, 28 of the measurement values 10 of the second measurement value set 6. The determined statistical spreads 13, 14, 15, 16 are subsequently compared with one another relative to predeterminable thresholds 21, 22, 23, 24 in four threshold comparisons. In the shown example, all statistical spreads 13, 14, 15, 16 are smaller than the predetermined thresholds 21, 22, 23, 24, such that a stable installation of the system 1 can be assumed and, if necessary, signaled to an operator.

By contrast, FIG. 4 shows two measurement value sets 7, 8 from the two measurement planes 29, 30 of the rotation device in the case of an unstable installation of the system 1.

In the case of an unstable installation of the system, the measurement values 11 and 12 of the respective measurement value sets 7 and 8 (again in FIG. 4 only one measurement value of the respective measurement value sets 7 and 8 is provided with a reference number) exhibit significantly higher statistical spreads 17, 18, 19, 20 relative to those of FIG. 3. The four statistical spreads 17, 18, 19, 20 of the measurement value components 27 28 (which statistical spreads 17, 18, 19, 20 are respectively formed from a difference) are significantly greater than the predetermined four thresholds 21, 22, 23, 24. In this case, the threshold comparisons lead to a detection of an unstable installation of the system 1.

Figure 5:
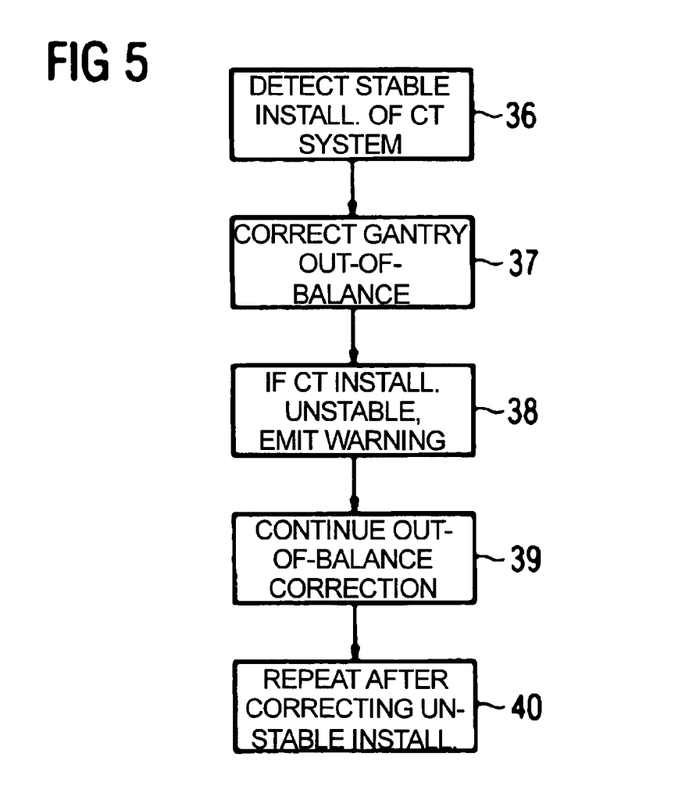
FIG. 5 is a flow chart of a first embodiment of the inventive method for detection of a stable installation of the computed tomography system of FIG. 2 as a part of a method for correction of an out-of-balance condition of the gantry thereof.

As shown in FIG. 5, the detection of a stable installation of a system 1, for example of a computed tomography system, can be used as a part of a method for detection and correction of an out-of-balance condition of the rotation devices thereof, for example a gantry. The following method steps are thereby implemented.

Step 36: detection of a stable installation of the computer tomograph.

Step 37: in the case of a stable installation of the computed tomography system, continuation of the correction of the out-of-balance of the gantry.

Step 38: in the case of an unstable installation of the computed tomography system, generation of a warning signal and acknowledgement of the warning signal by an operator, and implementing either step 39 wherein the correction of the out-of-balance condition is continued or step 40 wherein the method is repeated from step 36 after correction of the installation of the computed tomography system.

Figure 6:
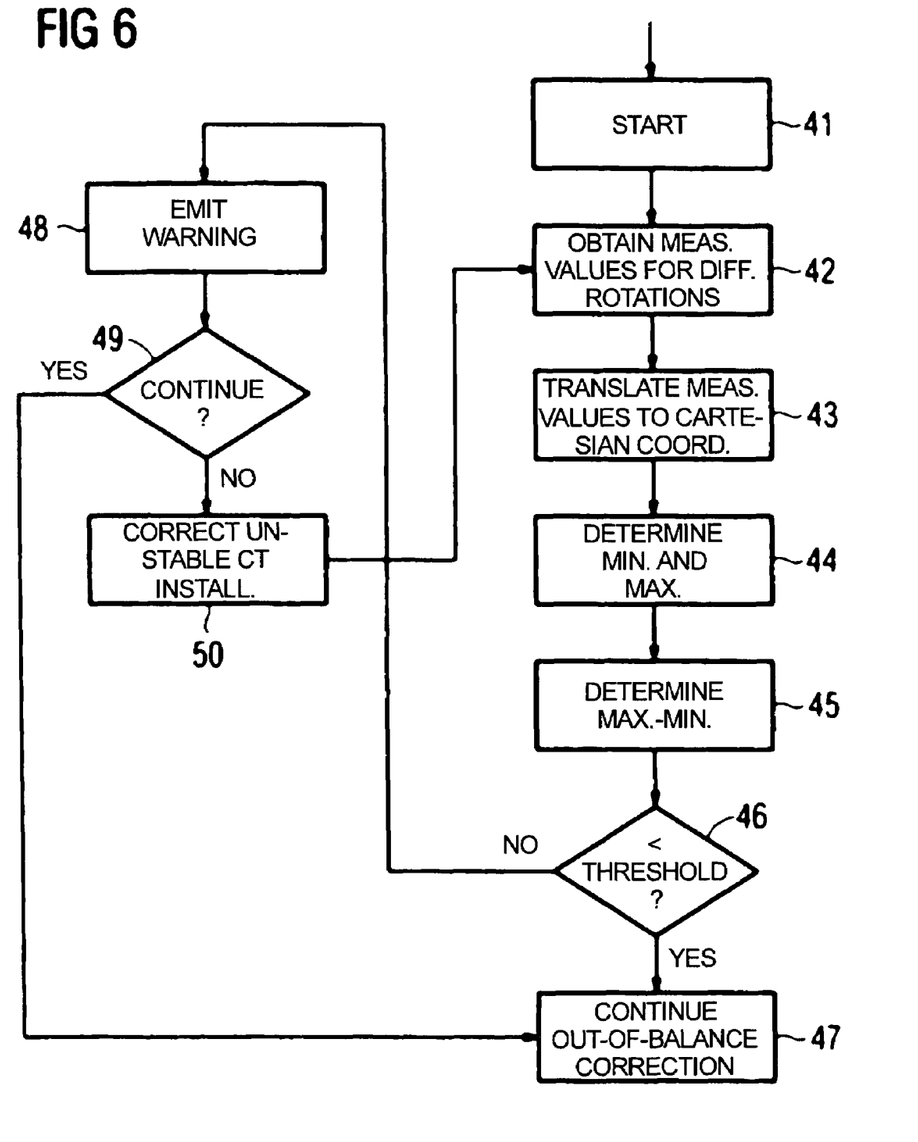
FIG. 6 is a flow chart of a second embodiment of the inventive method for detection of a stable installation of the computed tomography system of FIG. 2 as a part of a method for correction of an out-of-balance condition of the gantry thereof.

A more detailed embodiment of the method is shown in FIG. 6, in which the detection of the stable installation of the computed tomography system is a component of an out-of-balance measurement. The following method steps are thereby implemented.

The third method is started in step 41 by an operator, for example by calling a program stored in the computer 4. After the start, N measurement values of an out-of-balance measurement from N different rotations (wherein N is, for example, 10) are continuously recorded in at least one measurement plane in a second step 42. In a third step 43, the measurement values are subsequently translated into Cartesian coordinates. In a subsequent fourth method step 44, the minimum value and the maximum value of the respective measurement value components are determined. The statistical spread is subsequently calculated in a fifth step 45 from the difference of the maximum value and the minimum values of the respective measurement value components. In a sixth step 46, a threshold comparison is made to determine whether the statistical spreads in both coordinate directions are smaller than predeterminable limit values. If the threshold comparison leads to the result that both statistical spreads are smaller than the thresholds, the method for detection and correction of the out-of-balance condition is continued as usual in a seventh step 47. If one of the two statistical spreads be larger than the predetermined threshold, in an eighth method step 48 a warning signal (for example as an optical display on a screen) is generated with the instruction to check the installation of the computed tomography system. In a ninth step 49, the operator (for example by selection of an action item from a menu displayed on a screen) can either continue with the method for detection and correction of the out-of-balance condition according to the seventh method step 47, or can begin the detection of measurement values again according to the second step 42 after checking the installation of the computed tomography system in a tenth method step 50.

Although modifications and changes may be suggested by those skilled in the art, it is the intention of the inventor to embody within the patent warranted hereon all changes and modifications as reasonably and properly come within the scope of his contribution to the art.

I claim:

1. A method for detecting a stable installation of a system having a rotation device that is mounted to rotate around a system axis, and a detection arrangement that detects measurement values indicative of oscillation of said rotation device, said method comprising the steps of:

rotating said rotation device through a plurality of rotations and, with said detection arrangement, detecting at least one discrete measurement value in each of said different rotations of said rotation device, thereby obtaining a measurement value set comprising a plurality of said discrete measurement values;

for said measurement value set, automatically electronically determining a statistical spread of said a plurality of measurement values therein by determining a value separation among said discrete measurement values; and for said measurement value set, automatically electronically comparing the statistical spread thereof to a predetermined threshold, and thereby automatically electronically determining whether said system is supported in a stable manner if the calculated statistical spread for any measurement value set has a predetermined relationship to said threshold, and that said system is not supported in a stable manner if the calculated statistical spread for any measurement value set does not have said predetermined relationship to said threshold; and only if said system is determined not to be supported in a stable manner, generating a humanly perceptible warning signal.

2. A method as claimed in claim 1 comprising detecting two of said measurement value sets in each of two measurement planes that are perpendicular to said system axis and spaced from each other along said system axis.

3. A method as claimed in claim 2 comprising automatically electronically determining that said system is supported in a stable manner if either of said two measurement value sets is smaller than said threshold.

4. A method as claimed in claim 1 comprising detecting each of said a plurality of measurement values as a vector having two vector components, said two vector components comprising a first vector component representing a magnitude of an out-of-balance condition of said rotation device and a second vector component representing an angle of said out-of-balance condition of said rotation device.

5. A method as claimed in claim 4 comprising automatically electronically translating said first vector components into a Cartesian first measurement value component and automatically electronically translating said second vector component into a Cartesian second measurement value component.

6. A method as claimed in claim 5 comprising automatically electronically determining said statistical spread as a first statistical spread of said first measurement value component and a second statistical spread of said second measurement value component.

7. A method as claimed in claim 6 comprising automatically electronically calculating said first statistical spread as a maximum difference between any two of said first measurement value components for said a plurality of measurement values in each measurement value set.

8. A method as claimed in claim 6 comprising automatically electronically calculating said second statistical spread as a maximum difference between any two of said second measurement value components for said a plurality of measurement values in each measurement value set.

9. A method as claimed in claim 5 wherein said threshold comprises a first threshold component and a second threshold component, and wherein the step of automatically comparing said statistical spread to a predetermined threshold comprises automatically electronically comparing, for each measurement value set, a statistical spread of said first measurement value component to said first threshold component, and comparing a statistical spread of said second measurement value component to said second threshold component.

10. A method as claimed in claim 1 comprising mounting said detection arrangement in an imaging system containing said rotation device, and detecting said at least one measurement value set for said rotation device in said imaging system.

11. A method as claimed in claim 1 comprising mounting said detection arrangement in an computed tomography system containing said rotation device, and detecting said at least one measurement value set for said rotation device in said computed tomography system.

12. A method as claimed in claim 1 comprising representing each of said discrete measurement values as a graphical point, and determining said value separation among said discrete measurement values by determining a spacing among said graphical points.

13. A method for detecting a stable installation of a computed tomography apparatus having a gantry therein during a procedure for correction of an out-of-balance condition of said gantry, said gantry being mounted in said computed tomography system to rotate around a system axis, and said computed tomography system comprising a detection arrangement to detect measurement values indicative of oscillation of said gantry, said method comprising the steps of:

rotating said gantry through a plurality of rotations and, with said detection arrangement, detecting whether said computed tomography apparatus has a stable installation by detecting at least one discrete measurement value in each of said different rotations of said gantry, therein by determining a value separation among said discrete measurement values and, for said measurement value set, automatically electronically determining a statistical spread of said plurality measurement values therein by determining a value separation among said discrete measurement values and for said measurement value set, automatically electronically comparing the statistical spread thereof to a predetermined threshold, and automatically electronically determining that said gantry is supported in a stable manner if the calculated statistical spread for any measurement value set has a predetermined relationship to said threshold, and that said gantry is not supported in a stable manner if the calculated statistical spread for any measurement value set does not have said predetermined relationship to said threshold;

if said gantry is to be supported a stable, continuing said procedure for correction of an out-of-balance condition of said gantry; and only if said gantry is determined not to be supported in a stable manner, generating a humanly perceptible warning signal.

14. A method as claimed in claim 13 comprising allowing an operator of said computed tomography system, after generation of said warning signal, an option of continuing said procedure for correction of an out-of-balance condition of said gantry with said gantry not supported in a stable manner, or to continue with said procedure for correction of an out-of-balance condition of said gantry only after making an adjustment to said computed tomography system and repeating the step of detecting whether the computed tomography system has a stable installation to produce a result that said computed tomography system has a stable installation.

15. A method as claimed in claim 13 comprising representing each of said discrete measurement values as a graphical point, and determining said value separation among said discrete measurement values by determining a spacing among said graphical points.

* * * * *